(12) United States Patent
Mann

(10) Patent No.: US 7,261,907 B2
(45) Date of Patent: Aug. 28, 2007

(54) COMPOSITIONS FOR THE TREATMENT OF NEUROLOGICAL DISORDERS

(76) Inventor: Morris Mann, 21669 N. 57th Ave., Glendale, AZ (US) 85308

( * ) Notice: Subject to any disclaimer, the term of this patent is extended or adjusted under 35 U.S.C. 154(b) by 0 days.

(21) Appl. No.: 11/215,719

(22) Filed: Aug. 30, 2005

(65) Prior Publication Data

US 2005/0287229 A1   Dec. 29, 2005

Related U.S. Application Data

(62) Division of application No. 10/127,054, filed on Apr. 19, 2002, now abandoned.

(60) Provisional application No. 60/289,009, filed on May 4, 2001.

(51) Int. Cl.
| | |
|---|---|
| *A61K 47/44* | (2006.01) |
| *A61K 9/00* | (2006.01) |
| *A61K 9/10* | (2006.01) |
| *A61K 33/04* | (2006.01) |
| *A61P 25/18* | (2006.01) |
| *A61P 25/22* | (2006.01) |
| *A61P 25/24* | (2006.01) |
| *A61P 25/34* | (2006.01) |

(52) U.S. Cl. .................. 424/705; 424/400; 424/703; 424/713; 424/714; 514/762; 514/768; 514/785; 514/786; 514/810; 514/813; 514/937; 514/970

(58) Field of Classification Search .............. 514/785, 514/786, 810–813, 879, 762, 768, 937, 970; 424/400, 703, 705, 713, 714
See application file for complete search history.

(56) References Cited

U.S. PATENT DOCUMENTS 4,416,869 A    11/1983   Revici .................... 424/164

OTHER PUBLICATIONS

BIOSIS Abstract, accession No. 2003:294981 (2003).*
MEDLINE Abstract, accession No. 2002437929 (2002).*
MEDLINE Abstract, accession No. 1999278960 (1999).*
Chemical Abstracts 103:11231 ( 1985 ).

* cited by examiner

*Primary Examiner*—John Pak
(74) *Attorney, Agent, or Firm*—The Halvorson Law Firm

(57) ABSTRACT

A non-stoichiometric clathrate of lipid and sulfur has been shown to effectively stabilize nerve cell membranes. As such, said compound has proven useful in a variety of neuropsychiatric disorders such as, addiction, depression, autism, Tourette's syndrome, and the like.

5 Claims, 1 Drawing Sheet

COMPOSITIONS FOR THE TREATMENT OF NEUROLOGICAL DISORDERS

CROSS REFERENCE TO RELATED PATENTS

This applicant is a divisional application based on original application Ser. No. 10/127,054, filed on Apr. 19, 2002, now abandoned, which claims the benefit of U.S. Provisional Application No. 60/289,009, filed on May 4, 2001.

FIELD OF THE INVENTION

The invention relates to a unique composition that can be effectively used to treat a variety of neurological and psychiatric diseases.

BACKGROUND OF THE INVENTION

Dr. Emanuel Revici in his book *Research in Physiopathology as a Basis of Guided Chemotherapy* described a method of preparing sulfur. His process involved the formation of hydropersulfides. He also described the use of other sulfur containing compounds such as; alkyl sulfides, colloidal sulfur, organic thio compounds and their pharmaceutically acceptable salts such as ethylene trithiocarbonate, thioglyceraol, thioglycol, and the like.

Utilizing a different method of preparation of a substance was formed that has no evidence of ionic bonding, but instead has physical characteristics that constitute by definition a liquid crystal. The reaction itself is non-stoichiometric. The resulting compound is best described as a non-stoichiometric clathrate with no evidence of ionic bonding. As a result, this unique compound has broad effects on neurophysiology that could not have been predicted by analysis of prior art.

SUMMARY OF THE INVENTION

A proprietary technique was used to create a non-stoichiometric clathrate of lipid and sulfur. The lipid used was a medium chain triglyceride. However, many different aliphatic compounds or combinations of aliphatic compounds can be used without deviating from the spirit of the invention. In all cases, a compound was generated that showed no evidence of ionic bonding. Said compound is amenable to ingestion by mammals when mixed with appropriate binders and filling agents and thereafter encapsulated. Effective dosage and time necessary for a perceptible positive effect to occur seem to be directly related to the amount of neural tissue involved in a given neurological problem. This ranges from 100 mg or less to 2.5 grams or more in divided doses of the active substance as previously described.

The novel features that are considered characteristic of the invention are set forth with particularity in the appended claims. The invention itself, however, both as to its structure and its operation together with the additional objects and advantages thereof will best be understood from the following description of the preferred embodiment of the present invention when read in conjunction with the accompanying figures. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DESCRIPTION OF THE PREFERRED EMBODIMENTS

Figure 1:
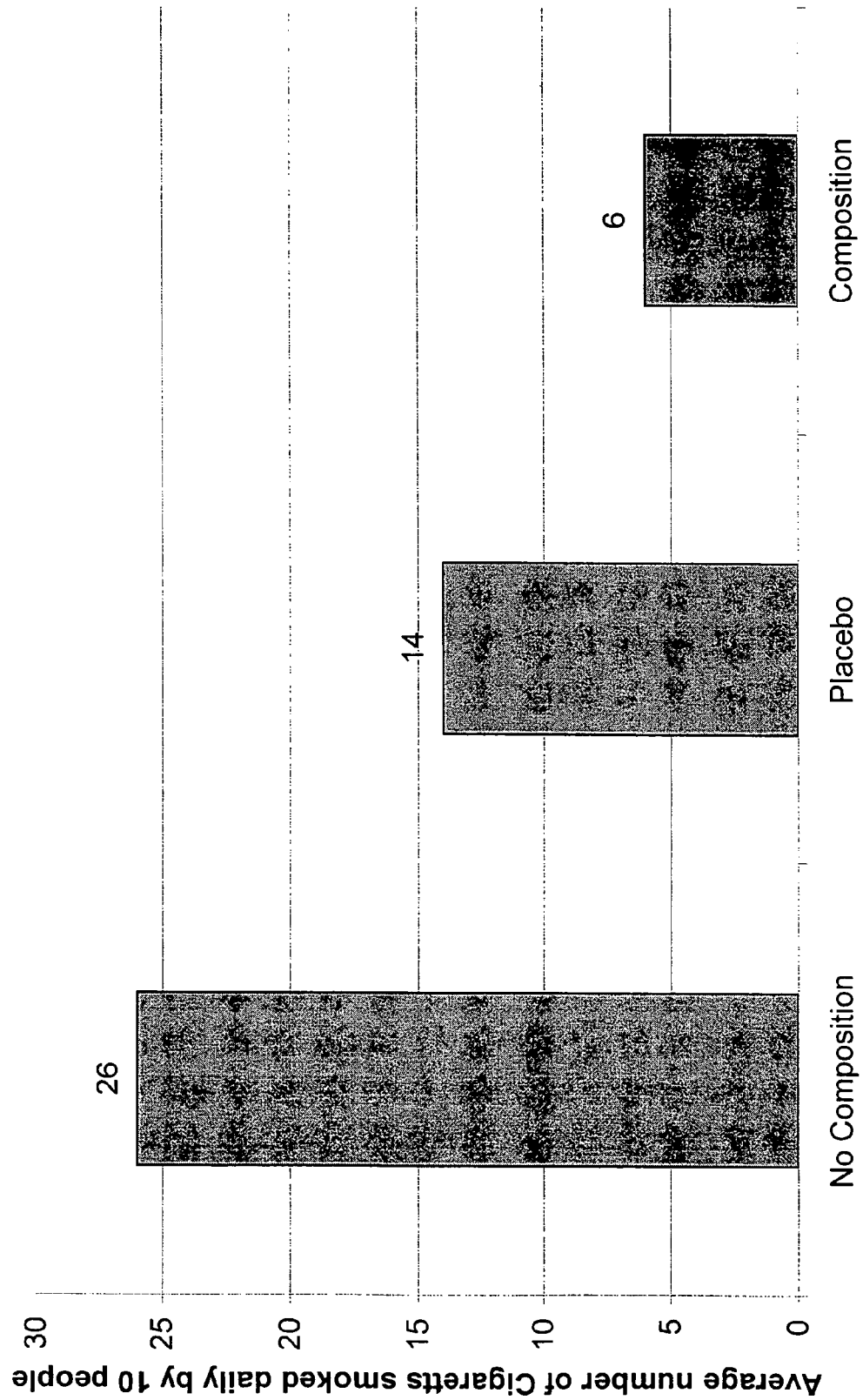
FIG. 1 shows the results of administration of the composition according to the present invention as follows: 120 mg at night, 120 mg in the morning and additional 60 mg doses as necessary till the individual did not want to smoke.

The present invention is a composition and method useful for the treatment of neurological disorders.

Addiction to water soluble substances such as nicotine, heroin, cocaine, and the like involves complex receptor site phenomena with progressive destabilization of nerve cell membranes and attendant defects in ionic flow through said membranes. With the tachyphylaxis that invariably occurs with addiction, cell membranes become progressively destabilized. The end result is a physiological craving for the substance of abuse. Previously, the water soluble antidepressant bupropion hydrochloride has proven to be moderately effective in treating nicotine and cocaine addiction. However, surprisingly, a lipidic clathrate of sulfur is astonishingly effective at reducing the required cigarette intake of chronic smokers and treatment of other neurological disorders. The mount of active agent required to produce this effect in chronic smokers averages 500 mg daily.

Sulfur is known to exist in three forms. The most common is cyclo-octa sulfur, a crystal of the orthorhombic space group commonly seen in nature. The other two are known as beta sulfur and gamma sulfur. Whereas cyclo-octa sulfur (alpha sulfur) is stable under normal atmospheric conditions; i.e. standard temperature and pressure, beta sulfur and gamma sulfur are not. In fact, beta and gamma sulfurs, which are crystals of the monoclinic space group, are inherently unstable. It has been found, however, that in the process of changing alpha sulfur to gamma or beta sulfur, in the presence of aliphatic materials, the aliphatic material is encapsulated by the sulfur crystal structure thereby creating a novel clathrate. This novel clathrate induces extremely long term stability in an otherwise unstable crystalline structure. It is also what allows the composition to have its apparent physiological effects, as described below. The composition is beta sulfur clathrate containing aliphatic materials. It forms pale yellow crystalline needles with a defined melting point of 119.6° C. This is the melting point of normal beta sulfur monoclinic crystals.

The compound was analyzed by a variety of different techniques. These included mass spectroscopy, infrared spectroscopy, high-pressure liquid chromatography, and X-ray crystallography. On no occasion was there any evidence of an ionic bond. Nor for that matter was there any evidence that the sulfur had formed organic bonds with the lipidic material. Therefore, by definition, the compound is a non-stoichiometric clathrate, a compound formed by the inclusion of molecules of one kind in cavities of the crystal lattice of another.

Ten individuals with long histories of chronic cigarette smoking were interviewed relative to their smoking habits. They were asked to track and count their cigarette use on a daily basis for two weeks. They were then given the composition in an encapsulated form or a placebo for four weeks. They were asked once again to track their cigarette intake. The results are illustrated in FIG. 1.

As can be seen from FIG. 1, composition was clearly more effective than either no treatment or treatment by the placebo. The average number of cigarettes smoked by 10 individuals receiving no treatment was 26. When treated with a placebo, the average number of cigarettes smoked by 10 individuals dropped to 14; nearly half that smoke by those receiving no treatment. Surprisingly, however, when treated with the sulfur/lipid clathrate according to the present invention, the average number of cigarettes smoked by 10 individuals dropped to 6. Unexpectedly, there is more than a four-fold decrease compared to individuals receiving no treatment and more than a two-fold decrease compared to individuals receiving a placebo.

Three individuals with long defined psychiatric histories of depression were given the composition. The results were quite unexpected.

In case 1, a 40 year old female with a long history of manic depression received a single dose of 600 mg of the composition while in the manic phase. Within 12 hours her affect was normal. One week after this single dosage, she became manic again. Treatment was administered and once again affect became normal within 12 hours.

In case 2, a 35 year old female with a history of chronic depression since age 15 was give a dosage of 400 mg at night and 200 mg in the morning. Within one week of initiation of treatment, she no longer had sustained depression and was able to wake up and immediately go to work. Episodes of non-situational crying ceased entirely.

In case 3, a 51 year old female with a more than 40 year history of anxiety and situational depression was given a single 400 mg dose of the composition. After administration of the single dose, anxiety was greatly diminished and a second dose of 400 mg was administered. The second dose eliminated all non-specific anxiety allowing her to focus on designated tasks without difficulty. The effects of these two doses were still apparent to the test subject four days later.

As demonstrated above, depression, especially the manic phase of manic depression requires doses of between 800 and 1600 mg/day. However, surprisingly, the manic phase is eliminated within 36 hours from the initiation of treatment in the vast majority of patients treated.

Anxiety states respond very well to this compound. Effective treatment results from as little as 400 mg/day. Subsequently chronic use will allow the dosage to diminish to 100 mg/day or less. Surprisingly, there are no side effects associated with the use of this compound; i.e. drowsiness, discoordination, slurred speech, and the like. The Hamilton anxiety scale test was used on 10 patents and showed favorable results.

Tourette's syndrome and autism are more serious neuropsychic disorders representing uncontrolled neurological activity. The dosage required to treat these disorders is considerably higher and there is a significantly longer latent period prior to the observation of favorable effects from the administration of the compound. The average dose for Tourette's syndrome is 1.6 gm/day, with a latent period of approximately 10 days. With autism, the average dose is 2.5 gm/day with a latent period of approximately 3 weeks.

Clearly, this compound is effective for neurological disorders that are characterized by inappropriate neural activity. Surprisingly, Attention Deficit Disorder also responds to this therapy. The dose ranges from 200 to 800 mg daily and surprisingly with chronic use, the dose can be decreased to between 100 to 300 mg/day.

While it is clear that the compound has many effects in what appears to be distinct disease entities, it should be noted that all said entities have in common a destabilized nervous system. Therefore, it will be appreciated by one skilled in the art that many other disease entities that reflect instability of the nervous system would respond favorably to this compound. Concomitantly, it should be appreciated that numerous modifications of said compound, such as changing the lipid or the sulfur source do not reflect substantive changes in the character or effect of the compound. As such, one skilled in the art could effect said changes without deviating from the true spirit and scope of the invention.

The preferred embodiment of the invention is described above in the Figures and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A method for the treatment of anxiety or manic-depressive condition comprising the step of administering to an animal subject in need thereof an effective amount of a composition comprising a clathrate of aliphatic material and monoclinic sulfur, wherein the aliphatic material is encapsulated by the monoclinic sulfur.

2. The method according to claim 1, further including the step of generating the clathrate of aliphatic material and monoclinic sulfur prior to the step of administering the clathrate to the subject.

3. The method of claim 1 wherein the aliphatic material is a lipid or lipids.

4. The method of claim 1 wherein the monoclinic sulfur is beta sulfur and the aliphatic material is a lipid or lipids.

5. The method of claim 1 wherein the animal subject is a human subject.

* * * * *